(12) United States Patent
Vetter et al.

(10) Patent No.: US 8,494,612 B2
(45) Date of Patent: Jul. 23, 2013

(54) INCREMENTAL REAL-TIME RECORDING OF TRACKED INSTRUMENTS IN TUBULAR ORGAN STRUCTURES INSIDE THE HUMAN BODY

(75) Inventors: Marcus Vetter, Edingen (DE); Ivo Wolf, Wiensenbach (DE); Ingmar Wegner, Heidelberg (DE); Hans-Peter Meinzer, Heidelberg (DE); Heinrich Becker, Heidelberg (DE)

(73) Assignees: Deutsches Krebsforschungszentrum, Heidelberg (DE); Thoraxlinik Heidelberg GmbH, Heidelberg (DE)

( * ) Notice: Subject to any disclaimer, the term of this patent is extended or adjusted under 35 U.S.C. 154(b) by 1189 days.

(21) Appl. No.: 10/590,195

(22) PCT Filed: Mar. 3, 2005

(86) PCT No.: PCT/EP2005/002244
§ 371 (c)(1),
(2), (4) Date: Apr. 25, 2007

(87) PCT Pub. No.: WO2005/084571
PCT Pub. Date: Sep. 15, 2005

(65) Prior Publication Data
US 2008/0033452 A1 Feb. 7, 2008

(30) Foreign Application Priority Data
Mar. 3, 2004 (DE) .......................... 10 2004 010 952

(51) Int. Cl.
*A61B 5/05* (2006.01)
*A61B 19/00* (2006.01)

(52) U.S. Cl.
USPC ........... 600/424; 600/407; 600/426; 600/438; 600/443; 600/459; 606/130

(58) Field of Classification Search
USPC ................. 600/160, 407, 424, 426, 427, 443, 600/445; 606/41, 130
See application file for complete search history.

(56) References Cited

U.S. PATENT DOCUMENTS

| | | | |
|---|---|---|---|
| 5,817,022 A * | 10/1998 | Vesely | 600/443 |
| 5,928,137 A * | 7/1999 | Green | 600/160 |
| 6,233,476 B1 | 5/2001 | Strommer et al. | |
| 6,423,009 B1 * | 7/2002 | Downey et al. | 600/461 |
| 6,473,635 B1 | 10/2002 | Rasche | |
| 7,115,124 B1 * | 10/2006 | Xiao | 606/41 |
| 7,844,320 B2 * | 11/2010 | Shahidi | 600/424 |
| 2002/0044631 A1 | 4/2002 | Graumann et al. | |
| 2002/0172328 A1 * | 11/2002 | Dekel | 378/205 |
| 2008/0319268 A1 * | 12/2008 | Michaeli et al. | 600/202 |

FOREIGN PATENT DOCUMENTS

| | | |
|---|---|---|
| DE | 102 10 645 A1 | 10/2003 |
| EP | 1 391 181 A1 | 2/2004 |

OTHER PUBLICATIONS

Stanley, "Prognostic Factors for Survival in Patients with Inoperable Lung Cancer," JNCL. vol. 65, No. 1, Jul. 1980, pp. 25-32.
Harms et al., "Contemporary Role of Modern Brachytherapy Techniques in the Management of Malignant Thoracic Tumors," Seminars in Surgical Oncology, 2001, pp. 57-65.
Schwartz et al., "Electromagnetic Navigation During Flexible Bronchoscopy," Respiration, 2003, pp. 516-522.
Wolf et al., "The Medical Imaging Interaction Toolkit (MITK)"—A Toolkit Facilitating the Creation of Interactive Software by Extending VTK and ITK," Proc. Of SPIE vol. 5367, 2004, pp. 16-27.
Vetter et al., "Navigation Aids and Real-Time Deformation Modeling for Open Liver Surgery," Proc. Of SPIE vol. 5029, 2003, pp-58-68.
Schobinger et al., "Robuste Analyse von GefaBstrukturen Basis Einer 3D-Skelettierung," 2003, pp. 76-80.

* cited by examiner

Primary Examiner — Robert Chen
Assistant Examiner — Baisakhi Roy
(74) Attorney, Agent, or Firm — Foley & Lardner LLP

(57) ABSTRACT

The invention relates to a method for navigation during medical interventions on tubular organ structures, characterized in that, before the intervention, static image data of the tubular organ structures are recorded and stored, the tubular organ structures are extracted from the image data and their course is converted into a geometric description used during the medical intervention for instrument/organ recording, and the instrument that is spatially localized by a tracking system is successively corrected in relation to the static data, by a transformation that is preferably defined by an optimization method, taking into account the geometric description and information on the previous distance covered by the instrument, or, conversely, the static data are successively corrected in relation to the instrument position, and thus the position of the instrument is associated with the anatomical structures in the static image data.

29 Claims, No Drawings

INCREMENTAL REAL-TIME RECORDING OF TRACKED INSTRUMENTS IN TUBULAR ORGAN STRUCTURES INSIDE THE HUMAN BODY

CROSS-REFERENCE TO RELATED APPLICATIONS

This application is the National Phase of PCT/EP2005/002244, filed Mar. 3, 2005, and published as WO 2005/084571, which in turn claims priority from German Patent Application No. 10 2004 010 952.4, filed Mar. 3, 2004, the contents of all are hereby incorporated by reference.

The invention relates to a method permitting more objective and more precise navigation during medical, diagnostic and therapeutic interventions on non-osseous, tubular organ structures.

BACKGROUND OF THE INVENTION

In recent years, an increasing incidence of adenocarcinomas and of more peripheral bronchial carcinomas has been observed, among other reasons due to changes in smoking habits (Stanley K. E., 1980, J. Natl. Cancer Inst, volume 65, pages 25-32). A highly promising radiotherapeutic approach lies in the introduction of stereotactic irradiation of the lungs. A disadvantage of this method, however, is the extensive technical outlay and time required (general anesthesia under high-frequency jet ventilation). Another approach lies in using navigated endoluminal irradiation by means of brachytherapy (Harms et al., 2001, Semin. Surg. Oncol., volume 20, pages 57-65). In the latter, a radioactive emitter is inserted through a catheter and placed directly in the tumor for a planned period of time. Because of the steep dose decline of the radiation source (Ir192), high-conformity dose distributions can be achieved which make it possible to protect surrounding normal tissue and to deliver high doses to tumors. Hitherto, brachytherapy could be used only for central forms of bronchial carcinoma. For this purpose, the irradiation catheter is introduced by a lung specialist with the aid of conventional bronchoscopy. Because of the extensive ramification of the bronchial tree and the associated problem of finding the correct path to more peripheral lung tumors, it has hitherto been possible to perform endoluminal irradiation only on tumors up to the 2nd level of segmental bronchi. This problem can be addressed by using an electromagnetic navigation system which, during the bronchoscopy, reveals the path to the more peripheral regions. Electromagnetic tracking systems with very small receiver coils that localize the catheter tip without direct viewing are already commercially available (e.g. AURORA, Northern Digital Inc., Waterloo, Ontario, Canada) and have already shown a high level of target accuracy. However, they have to be developed further in respect of their use in constantly moving soft-tissue parts, for example the lungs, and of the display of a pre-planned path to the target. Bronchoscopy navigation based on image data from computer tomography (CT) is known from the prior art (Superdimension, Herzliy, Israel, Schwarz et al., 2003, Respiration, volume 70, pages 516-522). However, the continuous ventilation of the lungs and the associated translocation of the bronchial tree make it much more difficult to determine the exact spatial relationship between the catheter tip and the bronchial tree. The approach of detecting the respiratory movement by means of markers applied to the chest and of taking this movement into account in position determination, leads to unsatisfactory results in the clinical application of this system. Particularly in the periphery of the bronchial tree, the system needs improving in terms of its precision, so that a combination of video image and virtual mapping sought by the physician is permitted. Here, it is not just the initial position of the irradiation catheter that is of interest, but also how its position is controlled throughout the treatment period.

In medical, diagnostic and therapeutic interventions on non-osseous, tubular organ structures, for example the blood vessels and bronchi of the human body, imaging methods have hitherto been used, for example high-intensity fluoroscopy, which always expose the patient and the treating physician to a radiation burden. Initial trials in navigation of tracked instruments, for example catheters or bronchoscopes, in non-osseous, tubular organ structures, are not adequate, in terms of their precision, for replacing these radiological imaging methods during the intervention.

In navigation in non-osseous, tubular organ structures, for example in navigated bronchoscopy, only external artificial or anatomical landmarks, or a small number of internal artificial or anatomical landmarks, have hitherto been used for recording a tracked instrument, for example a catheter or bronchoscope, using medical imaging data. Here, the skeleton of a tubular organ structure is not used for the recording in a catheter or bronchoscope.

Because of movements related to respiration within the thorax and abdomen, there is substantial organ displacement and deformation of the affected regions.

Registration points on the patient, or a small number of landmarks within the bronchus or a blood vessel, are not sufficient to ensure real-time recording of the tracked catheter or bronchoscope with previously recorded image data from computer tomography (CT) or magnetic resonance tomography (MRT). In bronchoscopy, for example, registration errors occur which make it difficult to perform reliable image-based tissue removal (biopsy) or intrabronchial irradiation and which increase the risk to the patient.

DESCRIPTION OF THE INVENTION

It is an object of the present invention to make available a navigation method with which real-time recording in tubular organ structures of the human body can be greatly improved.

As a solution, the invention proposes first segmenting the tubular structures from the three-dimensional or multi-dimensional image data (CT, MRT) obtained before the intervention, and then convert these into a graphic representation by means of known skeletonization techniques. In doing so, the center line of the tubular organ structure represents the edge of the graph.

During the intervention (e.g. biopsies or irradiation of the lungs), the patient is first roughly recorded by using the patient's internal and external landmarks.

The position of the instrument, for example of a catheter in vessels or of a bronchoscope in bronchoscopy, is spatially determined by a tracking system during the intervention. After the rough recording has been carried out, the path of this tracked instrument, relative to the external and possibly internal markers, in the tubular structure is followed. The position of the instrument is projected by a transformation rule onto the skeleton (model) of the tubular organ structure. Where the tubular organ structure has curves or ramifications, the model can be successively modified by a non-rigid transformation, such that the position of the catheter comes to lie at all times within the tubular organ structure. During the advance movement, a cost function determines the most probable model section on which the instrument is located. The displacements of the tubular organ structure, for example those related to respiration, lead to the spatial movement of the instrument.

The components orthogonal to the course of the tubular organ structure are used to correct the model.

In this way, it is possible for tubular organ structures to be recorded very exactly and in real time in the area of the instrument. The recording in this case takes place successively along the path of the instrument.

The method is comparable to the local position correction in GPS-aided motor vehicles which use direction and distance, i.e. speed and time, to carry out a comparison with the electronic map and use the intersections and curves for position correction. In the pictorial comparison in navigation in tubular organ structures, the "map", i.e. the skeleton or model of the tubular organ structure, is additionally distorted in the orthogonal movement to the street direction.

The advantage of the solution according to the invention is that the position of the tracked instrument is successively compared with the course of the tubular organ structure and, therefore, the model is adapted and the position of the instrument in relation to the structure is also determined (recording).

The advantage of the invention lies in the greatly enhanced accuracy of the recording in tubular organ structures, which accuracy can also be guaranteed during movements of the organ structure.

The marked improvement in the recording accuracy in vessels and bronchi improves existing navigation methods and opens up the possibility of new applications. Thus, high-intensity fluoroscopy procedures (angiography), which expose the patient and treating physician to a radiation burden, can be reduced. In addition, it is possible to achieve improved precision in the placement of vessel stents or in the placement of cardiac pacemaker electrodes.

Two or more trackers of a tracking system are applied to the patient's surface. The physician introduces the spatially tracked bronchoscopy tip into the trachea. Using the bronchoscopy camera, the position of the bronchoscope is compared with the position in the image data by the physician and is interactively assigned. The position of the bronchoscopy tip relative to the bronchial tree is then corrected according to the method described above. Thus, for example, a biopsy can be performed with precision on a lesion that has been identified in the pre-operative image data. A further application in oncological bronchoscopy concerns the positioning of irradiation probes within a bronchus.

The method according to the invention for navigation during medical interventions on tubular organ structures involves static image data of the tubular organ structures being recorded and stored before the intervention. The tubular organ structures are extracted from these image data and their course is converted into a geometric description. The latter is used during the medical intervention for instrument/organ recording, and the instrument that is spatially localized by a tracking system is recorded. This is done by taking into account the geometric description and information on the previous distance covered by the instrument. The transformation to be defined, which is preferably defined by an optimization method, is successively corrected in relation to the static data. It will be appreciated that, conversely, the static data can also be successively corrected in relation to the instrument position. Thus, the position of the instrument is associated with the anatomical structures in the static image data.

In particular, the information on the distance covered can represent the continuous recording of the spatial position of the instrument.

Preferably, only the instrument tip is recorded as the spatial position of the instrument.

It will be appreciated that the spatial position of the instrument can also be recorded by several positions or by an infinite number of positions, and thus continuously, along the instrument.

The information on the distance covered can contain further features, in particular ramifications and diameter of the tubular organ structures, which are recorded during the advance of the instrument.

The navigation method, and in particular the transformation method, can shape the static image data, such that the anatomical structures in the static image data match the anatomical structures of the patient at the instrument position.

The movement of the tubular organ structure can be calculated from the chronologically changing position of the instrument, in particular in the case of cyclical movements, for example the respiratory movements. The movement can be computed in particular from the components of the movement of the instrument that are orthogonal to the tubular organ structure.

In addition, a patient-specific or generalized movement model of the tubular organ structure and/or of the surrounding tissue can be used for position determination and for successive recording of the sensor in the tubular organ structure.

By taking the calculated cyclical movement into account, information on the profile and shape of the tubular structure itself can be obtained from the positions of the instrument over the course of time, in order to expand the static information on the tubular organ structure or, if appropriate, to complete this. It will be appreciated that this collated information can be used as static information at a later time, for example during therapy or a follow-up examination.

It will be appreciated that the successive recording of the sensor with the tubular organ structure does not have to take place continuously, and instead can, if appropriate, take place at certain times, for example at the start of the intervention.

The calculated movement of the tubular organ structure is taken into account in determining the transformation.

It will be appreciated that, by applying external or internal markers, the movement of the tubular organ structure can be recorded approximately and can be included in the calculation of the transformation.

It will also be appreciated that the transformation can be successively learnt along the distance covered.

Here, the geometric description represents the central lines and/or the ramifications and/or the surface of the tubular organ structure.

The invention is explained in more detail on the basis of the following examples, without being limited to these.

EXAMPLE 1

Navigated Bronchoscopy

Before the intervention, a skeleton model of the bronchial tree is generated in the manner described above, and the path to the target region is identified.

Two or more spatially detectable objects (trackers) of a tracking system are then applied to the patient's surface. The physician introduces the spatially tracked bronchoscopy tip into the trachea. Using the bronchoscopy camera, the position of the bronchoscope is compared with the position in the image data by the physician and is interactively assigned. The position of the bronchoscopy tip relative to the bronchial tree is then corrected according to the method described above. Thus, for example, a biopsy can be performed with precision on a lesion that has been identified in the pre-operative image data.

A further application in oncological bronchoscopy concerns the positioning of irradiation probes within a bronchus.

EXAMPLE 2

Sequence of an Examination

Using the Open Source Toolkit MITK (Medical Imaging Interaction Toolkit, Wolf et al. MITK, 2004, volume 5367, pages 16-27), the navigation system ARION (Augmented Reality for Intraoperative Navigation, Vetter et al., 2003, Navigation aids and real-time deformation modeling for open liver surgery, 2003, volume 5029, pages 58-68) is extended for bronchoscopy and brachytherapy. All the steps required for planning, calculation and implementation can be carried out with the developed application. First, the bronchial tree is extracted, with particular attention being paid to lower generations. The result is converted into a mathematical description (Schoebinger M. et al., 2003, in: BVM, pages 76-80). At the same time, an important region (carcinoma) for the operation can be segmented using interactive tools. Using 2D and 3D images of the bronchial tree and further segmentation, a lung specialist then interactively declares the start point and end point of the desired guide path, after which the calculated path is calculated from the mathematical description and immediately displayed. If desired, the result can be interactively changed. During the intervention, a commercially available electromagnetic tracking system (e.g. AURORA, NDI) is used to measure the position of the catheter tip. A new successive recording process improves the precision in the periphery of the lungs. The position of the catheter tip relative to the bronchial tree, the target bronchus and the path to it can now be displayed via 2D and 3D images. It is also possible, by augmented reality, to insert the target path into the bronchoscopy video image.

EXAMPLE 3

Representation of the Bronchial Tree

Initial trials on a movable lung model have shown that an improvement in precision is achieved by means of the successive recording. The tests are carried out for example with Aurora (NDI) and the MicroBird System (Ascension; Milton, Vt., USA). The mathematical representation of the bronchial tree permits rapid and interactive handling of the data. The view of the target path can be adapted to the preferences of the lung specialist. 2D sectional images and a 3D view of the bronchial tree with target path and the catheter tip are made available. A further point is that an image-assisted navigation system that permits fusion of bronchoscopy video image with target path represents a significant improvement for the lung specialist. The insertion of a conducting path can greatly improve the laborious and time-consuming search for the target region and can thus reduce the burden on the patient through shorter anesthesia times and may make it possible to dispense with CT controls for checking the position of the catheter. Even if the bronchoscope cannot reach further into the periphery because of its size, the improved recording means it is possible to convey the irradiation catheter further into the periphery by means of virtual bronchoscopy. For brachytherapy, this means improved determination of the position of the irradiation probe throughout the treatment period.

By means of the navigation system according to the invention, the lung specialist follows the path inserted virtually in the video image all the way to the target bronchus. Thus, for the first time, an image-based navigation aid for bronchoscopy and brachytherapy is made available. The involvement of the lung specialist in this is minimal, since only a thin path is plotted in the customary bronchoscopy image.

The invention claimed is:

1. A method for navigation during medical interventions on tubular organ structures with curves or ramifications, comprising:
    (a) recording and storing static image data of the tubular organ structures before the intervention,
    (b) extracting the tubular organ structures from the static image data,
    (c) converting a course of the tubular organ structures into a geometric description which is then used during the medical intervention for instrument/organ recording, wherein the geometric description represents at least one of the group consisting of central lines, ramifications, and surfaces of the tubular organ structures, and
    (d) spatially localizing the instrument position by a tracking system and successively correcting the instrument position in relation to the static image data, by a transformation that is defined by an optimization method which comprises:
        taking into account the geometric description, movement of the tubular organ structures, and information on previous distance covered by the instrument,
    wherein the movement of the tubular organ structures is calculated from a changing position of the instrument and thus, the position of the instrument is associated with the tubular organ structures in the static image data,
    wherein the information on the distance covered represents the continuous recording of a spatial position of the instrument and contains further features which represent ramifications of the tubular organ structures, and
    wherein the transformation is successively learned along the distance covered.

2. The method as claimed in claim 1, characterized in that the information on the distance covered represents the continuously recorded spatial position of the instrument.

3. The method as claimed in claim 2, characterized in that only the instrument tip is recorded as the spatial position of the instrument.

4. The method as claimed in claim 2, characterized in that several positions along the instrument are recorded as the spatial position of the instrument.

5. The method as claimed in claim 2, characterized in that the spatial position of the instrument is recorded continuously along the instrument.

6. The method as claimed in claim 2, characterized in that other parts of the organ tubular structure are recorded by registering the instrument position taking into account the calculated cyclical movements, wherein the cyclical movements, which can represent respiratory movements, of the tubular organ structure are calculated from the chronologically changing position of the instrument.

7. The method as claimed in claim 6, characterized in that the recorded collated infotmation can be used at a later time as static information.

8. The method as claimed in claim 1, characterized in that the information on the distance covered contains further features which can represent ramifications of the tubular organ structure.

9. The method as claimed in claim 1, characterized in that the transformation shapes the static image data.

10. The method as claimed in claim 1, characterized in that cyclical movements, which can in particular represent respiratory movements, of the tubular organ structure are calculated from the chronologically changing position of the instrument.

11. The method as claimed in claim 10, characterized in that the transfoiniation includes the calculated movements of the tubular organ structure.

12. The method as claimed in claim 1, characterized in that the movement of the tubular organ structure is computed from components of the movement of the instrument that are orthogonal to the tubular organ structure.

13. The method as claimed in claim 1, characterized in that, by applying external or internal markers, the movement of the tubular organ structure is recorded and included in the calculation of the transformation.

14. The method as claimed in claim 1, characterized in that the geometric description represents central lines of the tubular organ structure.

15. The method as claimed in claim 1, characterized in that the geometric description represents ramifications of the tubular organ structure.

16. The method as claimed in claim 1, characterized in that the geometric description represents a surface of the tubular organ structure.

17. The use of the method as claimed in claim 1 in bronchoscopy interventions.

18. The use of the method as claimed in claim 1 as a replacement for angiographic imaging in catheter interventions.

19. The use of the method as claimed in claim 1 in the implantation of cardiac pacemakers.

20. The use of the method as claimed in claim 1 for positioning of probes.

21. The use of the method as claimed in claim 1 for positioning of ablation electrodes.

22. The use of the method as claimed in claim 1 for positioning of stents in vessels and bronchi.

23. The use of the method as claimed in claim 1 for checking the position of a catheter.

24. The method as claimed in claim 1, characterized in that a generalized movement model of the tubular structure is taken into account in calculating the position.

25. The method as claimed in claim 1, characterized in that a generalized movement model of tissue surrounding the tubular organ structure is included in calculating the position.

26. The method as claimed in claim 1, characterized in that a patient-specific movement model of the tubular structure is taken into account in calculating the position.

27. The method as claimed in claim 1, characterized in that a patient-specific movement model tissue surrounding the tubular organ structure is taken into account in calculating the position.

28. The method as claimed in claim 1, characterized in that the recording is successively improved only at certain time intervals.

29. The method as claimed in claim 28, characterized in that all the information on the tubular structure is obtained from the recorded and movement-corrected instrument positions and is used as (quasi) static information.

* * * * *

UNITED STATES PATENT AND TRADEMARK OFFICE
CERTIFICATE OF CORRECTION

| | | |
|---|---|---|
| PATENT NO. | : 8,494,612 B2 | Page 1 of 1 |
| APPLICATION NO. | : 10/590195 | |
| DATED | : July 23, 2013 | |
| INVENTOR(S) | : Vetter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1498 days.

Signed and Sealed this
Twenty-fifth Day of August, 2015

Michelle K. Lee
*Director of the United States Patent and Trademark Office*